US012723966B2

(12) United States Patent
Yu et al.

(10) Patent No.: US 12,723,966 B2
(45) Date of Patent: Sep. 1, 2026

(54) DEVICE AND METHOD FOR EVALUATION PROTECTION PERFORMANCE USING DYNAMIC SWATCH TESTING CELL

(71) Applicant: AGENCY FOR DEFENSE DEVELOPMENT, Yuseong-gu (KR)

(72) Inventors: Seung Jung Yu, Yuseong-gu (KR); Hyun Sook Jung, Yuseong-gu (KR); Hee Soo Jung, Yuseong-gu (KR); Goon Hyeok Kim, Yuseong-gu (KR); Jae Heon Lee, Yuseong-gu (KR)

(73) Assignee: AGENCY FOR DEFENSE DEVELOPMENT, Yuseong-gu (KR)

( * ) Notice: Subject to any disclaimer, the term of this patent is extended or adjusted under 35 U.S.C. 154(b) by 331 days.

(21) Appl. No.: 18/231,555

(22) Filed: Aug. 8, 2023

(65) Prior Publication Data

US 2024/0053247 A1 Feb. 15, 2024

(30) Foreign Application Priority Data

Aug. 9, 2022 (KR) ........................ 10-2022-0099115

(51) Int. Cl.

| | |
|---|---|
| ***G01N 15/08*** | (2006.01) |
| ***G01N 1/22*** | (2006.01) |
| ***G01N 1/36*** | (2006.01) |
| *G01N 33/00* | (2006.01) |

(52) U.S. Cl.

CPC ........... *G01N 15/0826* (2013.01); *G01N 1/22* (2013.01); *G01N 1/36* (2013.01); *G01N 33/0057* (2013.01)

(58) Field of Classification Search

CPC .. G01N 15/0826; G01N 1/22; G01N 33/0057; G01N 2015/0026; G01N 33/36; G01N 2015/084; G01N 2015/086

USPC ............. 73/38, 861.47, 861.53, 861.67, 159, 73/863.56, 866, 865.6

See application file for complete search history.

(56) References Cited

U.S. PATENT DOCUMENTS 4,840,074 A * 6/1989 Jessop ..................... F16K 11/02 73/864.81

FOREIGN PATENT DOCUMENTS

| | | | | |
|---|---|---|---|---|
| CN | 103257086 A | * | 8/2013 | |
| CN | 214793658 U | * | 11/2021 | |
| JP | 2006300629 A | | 11/2006 | |
| JP | 6592721 B2 | | 10/2019 | |
| KR | 20150133420 A | | 11/2015 | |
| KR | 101700756 B1 | | 2/2017 | |
| KR | 101854139 B1 | | 5/2018 | |
| KR | 20190055646 A | | 5/2019 | |
| KR | 102514823 B1 | * | 3/2023 | ......... G01N 15/0806 |

* cited by examiner

*Primary Examiner* — Robert R Raevis

(74) *Attorney, Agent, or Firm* — Nixon Peabody LLP

(57) ABSTRACT

The present invention provides a practical protection performance test evaluation technology of CBRN protective clothing according to mass transfer characteristics of an aerosol, which is to break away from the existing static CBRN protection test cell and reflect an air flow around the CBRN protection and body motions of individual soldiers, and dynamically design a Swatch test cell in a geometric shape that can be installed inside a wind tunnel, and reflect an aerosol flow that can more closely simulate battlefield environment.

13 Claims, 10 Drawing Sheets

FIG. 4B
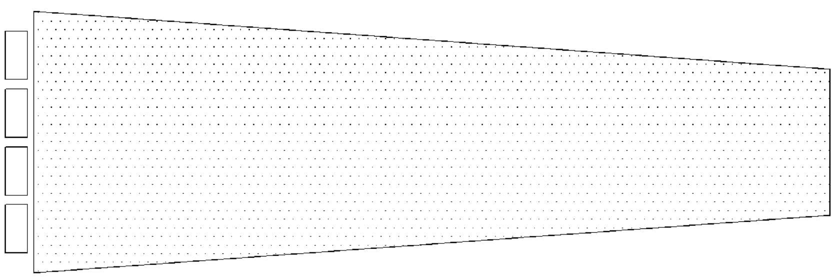
FIG. 4C
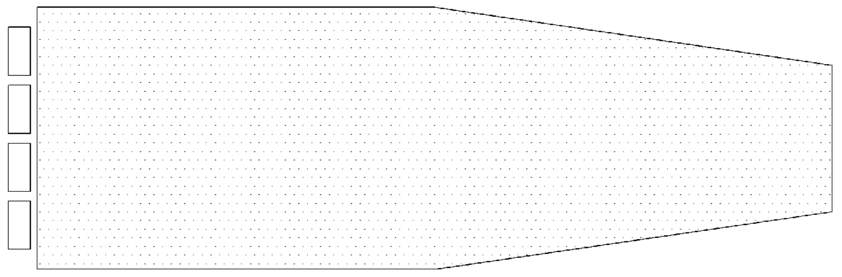
FIG. 4D
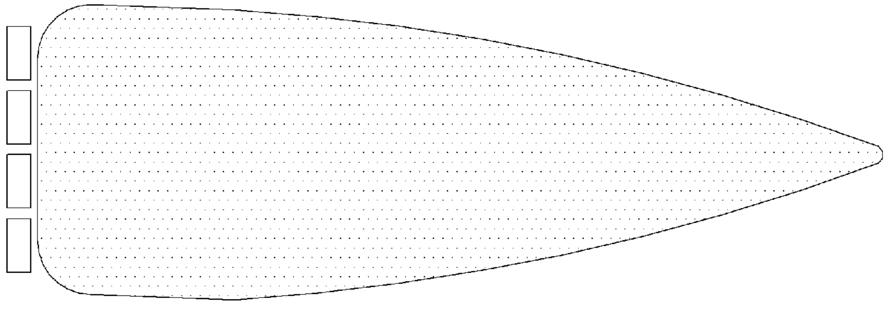
FIG. 5A

FIG. 7

| DIVISION | TEST CROSS - SECTIONAL AREA | RATIO OF TEST CROSS - SECTIONAL AREA TO WIND TUNNEL INLET AREA | WIND TUNNEL INLET/OUTLET DIFFERNTIAL PRESSURE | FABRIC INLET PRESSURE | FABRIC OULET PRESSURE |
|---|---|---|---|---|---|
| | $CM^2$ | % | Pa | Pa_g | Pa_g |
| MODEL 1 | 19.63 | 19.63 | 11.46 | 21.88 | -2.74 |
| MODEL 2 | 7.07 | 7.07 | 3.21 | 14.78 | -3.05 |
| MODEL 3 | 7.07 | 7.07 | 3.14 | 14.75 | 0.13 |
| MODEL 4 | 7.07 | 7.07 | 2.8 | 14.36 | -0.04 |
| DIVISION | FABRIC INLET/OUTLET DIFFRENTIAL PRESSURE | FACE VELOCITY | INFLOW FLOW RATE | PASSAGE FLOW RATE | PASSAGE FLOW RATE RATIO |
| | Pa | cm/s | g/s | g/s | % |
| MODEL 1 | 24.61 | 0.589 | 61.3 | 0.01416 | 0.02312 |
| MODEL 2 | 17.82 | 0.43 | 61.3 | 0.00373 | 0.00608 |
| MODEL 3 | 14.63 | 0.384 | 61.3 | 0.00333 | 0.00543 |
| MODEL 4 | 14.39 | 0.342 | 61.3 | 0.00333 | 0.00543 |

DEVICE AND METHOD FOR EVALUATION PROTECTION PERFORMANCE USING DYNAMIC SWATCH TESTING CELL

CROSS-REFERENCE TO RELATED APPLICATIONS

This application claims priority under 35 U.S.C. § 119 to Korean Patent Application No. 10-2022-0099115, filed on Aug. 9, 2022, in the Korean Intellectual Property Office, the disclosure of which is incorporated herein by reference in its entirety.

TECHNICAL FIELD

The following disclosure relates to a device and method for evaluating protection performance, and more particularly, to a device and method for evaluating protection performance for evaluating chemical or biological protection performance of protective clothing.

BACKGROUND

In the event of a chemical and biological weapons attack, chemical or biological agents may be a threat by being dispersed into the atmosphere and on the ground in various forms and phases, such as droplets, microparticles, aerosols, and vapors. The chemical, biological, radiological, and nuclear (CBRN) personal protection system for these chemical and biological agents, in particular, the protection performance evaluation technology of the current CBRN protective clothing is limited to the evaluation technology for vapor agents, and the protection performance evaluation technology for aerosols, particularly liquid aerosols, is insufficient. Liquid aerosols with a size of tens of nanometers to several micrometers may pose a greater threat due to secondary evaporation after penetration of CBRN protection, so it is necessary to develop a protection performance evaluation method for liquid aerosols of chemical agents in order to promptly respond to CBRN.

Chemical and biological agent aerosols exhibit complex mass transfer characteristics such as convection, diffusion, permeation, and bypass according to air flow, so it is necessary to reflect the flow of chemical and biological agent aerosols according to air flow in test evaluation techniques.

In addition, there is a risk that an individual soldier who performs operations on the battlefield after wearing CBRN protective clothing may be exposed to chemical or biological agent aerosol inflow from various angles by various body movements while performing various activities and aerosol (solid, liquid, vapor mixture) air contaminated from the outside flows into the inside of the protective equipment in a discontinuous area between the protective equipment, a dynamic protection performance evaluation technology that reflects and simulates body motions of individual soldiers is required.

RELATED ART DOCUMENT

Patent Document (Patent Document 0001) Japanese Patent Laid-Open Publication No. 2006-300629

SUMMARY

An embodiment of the present invention is directed to providing a device and method for evaluating protection performance using dynamic swatch testing cell for aerosols, particularly liquid aerosols in order to solve the problem that protection performance evaluation technology is limited to vapor phase agents.

The existing protection performance evaluation technology is based on evaluation of a fixed specimen and a fluid flowing in one direction, and the present invention provides a device and method for evaluating protection performance using dynamic swatch testing cell that can simulate a body motion of an individual soldier during battlefield activities which are difficult to implement in existing technologies, and can be introduced from various angles.

In one general aspect, a device for evaluating protection performance including a test unit in which a fluid flows in one direction includes: a specimen holder arranged in the test unit and having a specimen arranged at one end thereof; a support having one end coupled to the specimen holder and the other end coupled to the test unit, and including one or more rotation means; a plurality of collection tubes arranged at a front end of the specimen holder and inside the specimen holder; and a control unit controlling the support.

The rotation means may be formed of a multi-jointed arm or one or more hinges.

A turntable may be arranged at a lower end of the support.

The specimen holder may be formed in any one of a cylindrical shape, a truncated cone shape, a streamlined shape, and a mixed shape.

The collection tube may include a first collection tube arranged at the front end of the specimen holder and a second collection tube arranged inside the specimen holder, and the second collection tube may be made of a flexible material or a position may be changed by the control unit.

A rear end of the specimen holder may be connected to a connector coupled to a pump, and the control unit may be connected to a pump to control an internal pressure of the specimen holder.

The connector may be attached to and detached from the specimen holder.

The specimen holder may include a cover arranged to surround the specimen at one end and a cover removal device coupled to the test unit and pressing the cover.

The test unit may include rails formed in longitudinal and circumferential directions, and the cover removal device may be moved along the rails.

The cover removal device may include a guide coupled to the cover removal device, moved at a predetermined interval in the cover removal device, and pressing the cover.

In another general aspect, a method of evaluating protection performance includes: an arranging step in which a specimen holder having a specimen arranged at one end thereof is arranged in a test unit; and a measuring step in which a fluid flows in one direction in the test unit and a measuring unit measures a flow rate and a concentration of an agent through a collection tube arranged at a front end and an inside of the specimen holder, in which, in the arranging step, a control unit controls a support coupled with the specimen holder to change a position of the specimen holder.

The arranging step may include a cover coupling step in which the cover is arranged on a front surface of the specimen, and after the required environment in the test unit is created, the measuring step may include a cover removal step in which a cover removal device removes the cover.

The arranging step may include a face velocity control step in which the control unit controls a pump connected to a rear end of the specimen holder to adjust an internal pressure of the specimen holder and controls a face velocity of the fluid passing through the specimen.

In the measuring step, the control unit may control the support to change a position of the specimen holder.

BRIEF DESCRIPTION OF THE DRAWINGS

FIGS. 4A to 4D are exemplary diagrams of specimen holder deformation.

FIGS. 5A to 5E are exemplary diagrams of a flow analysis model according to a shape of a specimen holder.

FIG. 7 is a diagram illustrating result data according to each analysis model.

DETAILED DESCRIPTION OF MAIN ELEMENTS

| | | |
|---|---|---|
| 1: Test unit | | |
| 2: Specimen | | |
| 100: Specimen holder | | |
| 110: Support | 120: Turntable | 130: Cover |
| 200: Measuring unit | | |
| 210: First collection tube | 220: Second collection tube | |
| 300: Pump | | |
| 310: Connector | | |
| 400: Cover removal device | | |
| 410: Guide | 420: Rail | |
| A: Aerosol | | |

DETAILED DESCRIPTION OF EMBODIMENTS

The present invention may be variously modified and have several exemplary embodiments. Therefore, specific exemplary embodiments of the present invention will be illustrated in the accompanying drawings and be described in detail. However, it is to be understood that the present invention is not limited to a specific exemplary embodiment, but includes all modifications without departing from the scope and spirit of the present invention.

Unless indicated otherwise, it is to be understood that all the terms used in the specification, including technical and scientific terms have the same meaning as those that are understood by those skilled in the art to which the present invention pertains.

It should be understood that the terms defined by the dictionary are identical with the meanings within the context of the related art, and they should not be ideally or excessively formally defined unless the context clearly dictates otherwise.

Hereinafter, a device and method for evaluating protection performance using dynamic swatch testing cell according to an embodiment of the present invention will be described in detail with reference to the accompanying drawings.

Figure 1:
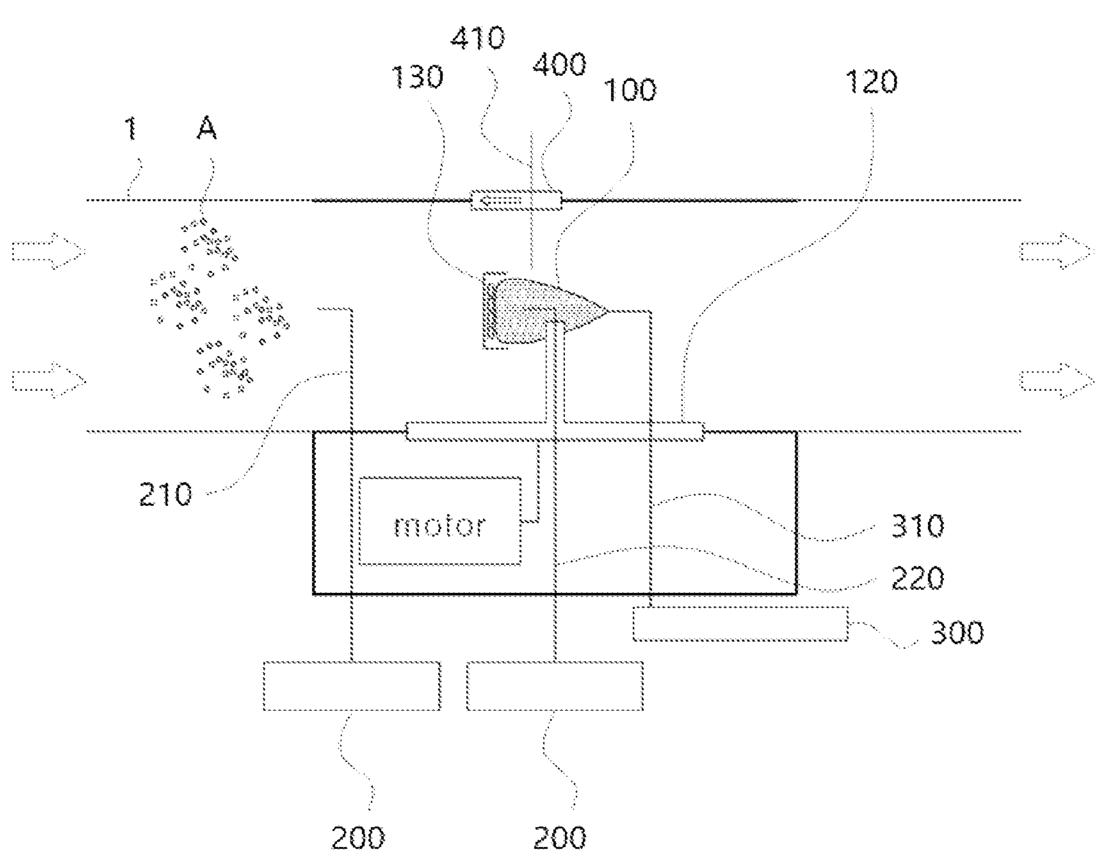
FIG. 1 is an overall conceptual diagram constituting one embodiment of the present invention.

FIG. 1 is an overall conceptual diagram constituting one embodiment of the present invention. Referring to FIG. 1, according to the present invention, a device for evaluating protection performance including a test unit 1 in which a fluid including an aerosol A flows in one direction includes a specimen holder 100 arranged in the test unit 1 and having a specimen arranged at one end thereof, a support 110 having one end coupled to the specimen holder 100, the other end coupled to the test unit, and including one or more rotation means, a first collection tube 210 arranged at a front end of the specimen holder 100 and a second collection tube 220 arranged inside the specimen holder 100, and a control unit controlling movement of the support 110.

The test unit 1 includes a space in which the fluid including the aerosol A flows in one direction. The test unit includes, for example, a wind tunnel and a wind tunnel test chamber. The test unit 1 is injected with aerosol or mixed steam to create a polluted environment. In the test unit 1, a CBRN protective clothing specimen and a specimen holder supporting the specimen are installed, and a number of measuring tubes are arranged to measure the concentration of aerosol.

In the specimen holder 100, a specimen is arranged at one end and spaced apart from an inner surface of the test unit 1 by the support 110. In the specimen holder 100, the size of the specimen and the shape of the specimen holder 100, such as geometric shape and size change according to test evaluation and required circumstances.

The support 110 coupled so that the specimen holder 100 is tilted or rotated is controlled by a control unit. The support 110 changes the position of the specimen holder 100 by including a rotation means. The rotation means is formed of a multi-jointed arm or includes a component such as a hinge. The components such as the multi-jointed arm or the hinge are controlled by the control unit. In the support 110, the specimen holder 100 is rotated by the turntable 120 connected to the motor. In this case, the turntable 120 and the motor are arranged inside the test unit 1 so as not to interfere with the flow of aerosol.

The control unit is connected to the support 110 and the turntable 120 to give movement such as tilting and rotation of the specimen holder 100, and can be controlled through remote control.

The present invention includes a measuring unit 200 for analyzing the aerosol or vapor concentration created in the test unit 1. One or more measuring units 200 are arranged, and are arranged outside the test unit 1 so as not to interfere with the flow of aerosol. The measuring unit 200 measures the test through a plurality of collection tubes, and is not limited to the number of collection tubes illustrated. The measuring unit 200 has a first collection tube 210 at a front end of the specimen and a second collection tube 220 at a rear end of the specimen through analysis of aerosol or vapor concentration penetrating the specimen to evaluate protection performance in units of specimen.

The first collection tube 210 arranged at the front end of the specimen measures a concentration of aerosol constituting the environment of the test unit 1. The first collection tube 210 is arranged at a center of a cross section of the test unit 1 and is arranged toward the direction in which the aerosol flows to measure the environment created in the test unit, or is arranged at the front end of the specimen to measure the concentration of aerosol immediately before passing through the specimen.

When the position reference of the first collection tube 210 is set to the front end of the specimen, a driving unit is further included to control the position of the first collection tube 210 to correspond to the movement of the specimen holder 100.

The second collection tube 220 is arranged at the rear end of the specimen, that is, inside the specimen holder 100, and measures the concentration of aerosol passing through the specimen. The specimen holder 100 moves by the movement of the support 110, and the second collection tube 220 is made of a material having flexibility to correspond to the movement of the specimen and specimen holder 100, or includes the driving unit.

The present invention does not limit the number of collection tubes arranged, and a differential pressure at an inlet and outlet of the test unit 1, the specimen inlet pressure, a specimen outlet pressure, a face velocity, an inflow amount, a passage flow rate, and a passage flow rate ratio, etc., are measured through a plurality of collection tubes. Through this, there is an advantage in reflecting complex mass transfer characteristics such as convection, diffusion, permeation, and bypass that aerosol may exhibit through data according to the position or shape of the specimen holder 100.

The present invention includes a face velocity control system. The specimen holder 100 is connected to a connector 310 connected to a pump 300 at the rear end to be attachable and detachable. The pump is arranged on the outside of the test unit, and the connector includes a flexible material or a driving unit to respond to the movement of the test holder. In the present invention, air is injected or sucked into the specimen holder 100 through the connector 310 to control the face velocity of the aerosol passing through the protective clothing. By controlling the face velocity, the aerosol protection performance suitable for the situation is evaluated.

For example, by controlling the internal pressure of the specimen holder 100 through the pump 300 and the connector 310, it is possible to simulate a relatively low internal pressure of clothing when waking up from a crouching state, and simulate a relatively high pressure inside the clothing when shrinking from standing up. In addition, the specimen changes to a convex or concave shape by injection or suction of the pump, so the test according to the shape deformation of the specimen may be performed.

A valve and a flow meter may be installed in the middle of the connector to control and measure the flow rate of aerosol entering the pump 300, and an appropriate filter such as a HEPA filter may be installed to block harmful substances entering the pump.

The present invention includes a cover removal system so that the test is performed after the internal environment of the test unit is created. It has the advantage of obtaining accurate test data through the cover removal system. Before the test, the cover 130 is arranged on the front of the specimen. The cover prevents aerosols from passing through and adhering to the specimen. After reaching the required environment in the test unit 1, the test is performed, and the cover removal device 400 for removing the cover is arranged to conduct the test.

The cover removal device 400 is arranged on an inner circumferential surface of the test unit 1, and presses the cover 130 to separate the cover 130 from the specimen holder 100. The cover removal system will be described later in detail with reference to FIG. 3.

Figure 2:
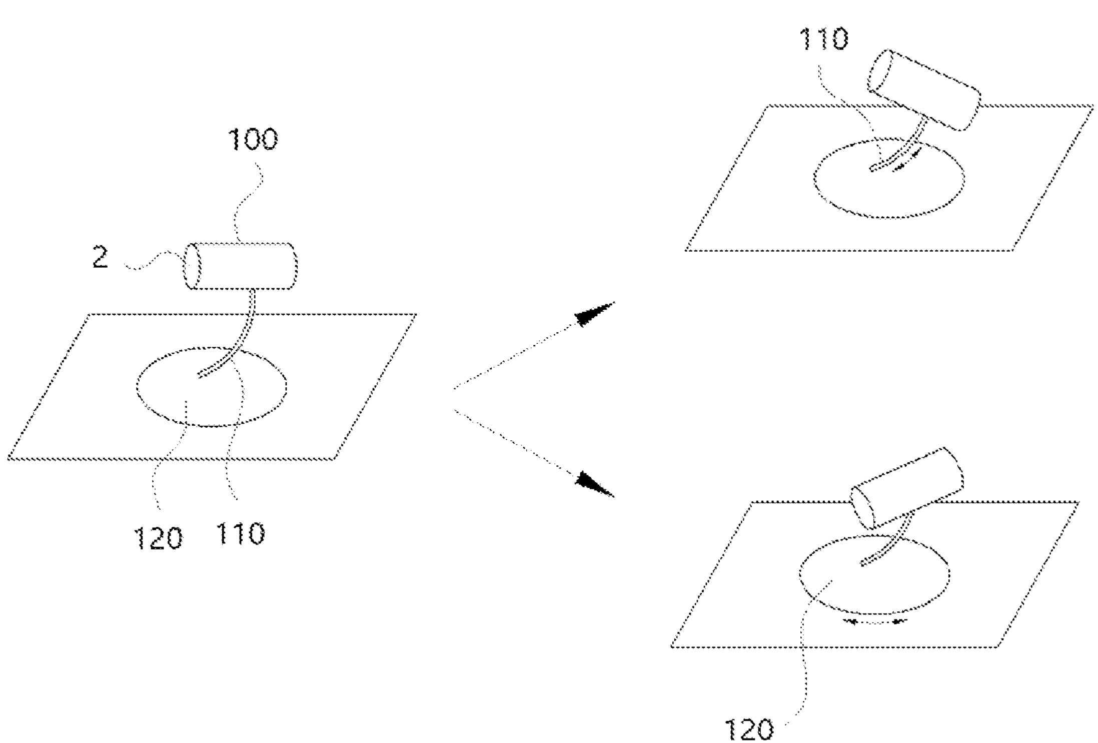
FIG. 2 is an exemplary motion diagram of a support.
Figure 8:
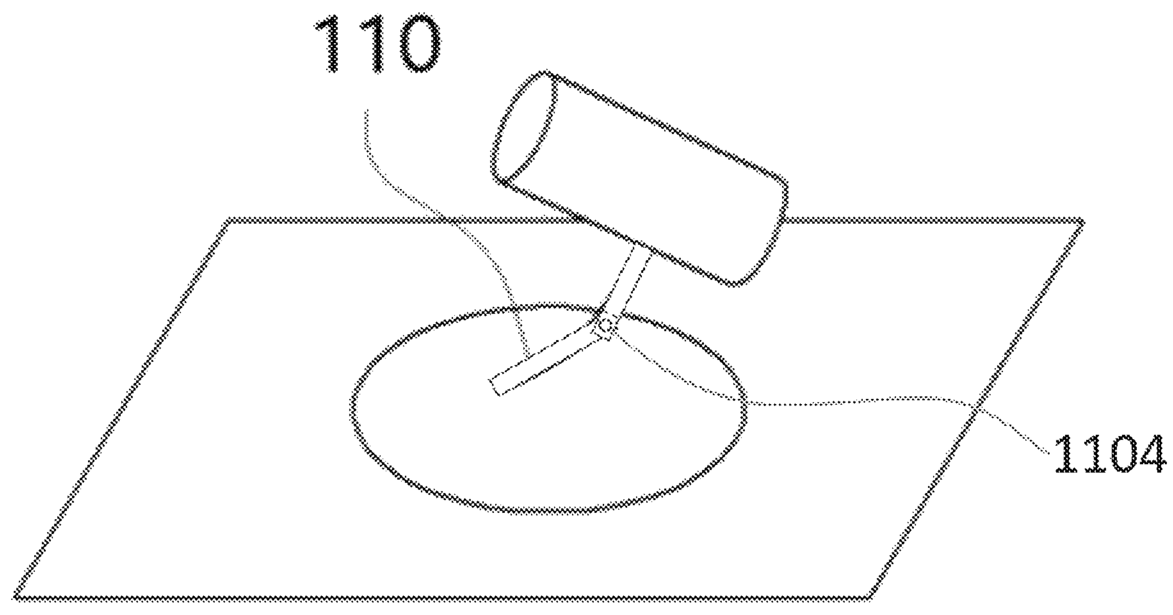
FIG. 8 is a schematic view of at least one hinge which is part of the support having one end coupled to the specimen holder and the other end coupled to the test unit.

FIG. 2 is an exemplary diagram of the movement of the specimen holder 100. Referring to FIG. 2, the specimen holder 100 is arranged in the test unit by the support 110. In the specimen holder 100, a protective clothing specimen 2 is arranged at one end, and performance evaluation is performed by aerosol injection. The support 110 includes a hinge 1104 (FIG. 8) so that the specimen holder 100 is tilted, and rotated by the turntable 120 arranged at the bottom of the support 110.

The support 110 and the turntable 120 are connected to the control unit, and the specimen holder 100 is tilted and rotated by a signal from the control unit. As the specimen holder 100 is tilted and rotated by the control unit within the test unit 1 through which fluid flows in one direction, there is an advantage in that simulation according to various environments is possible.

For example, the test is performed while the positions of the specimen 2 and the specimen holder 100 are tilted or rotated by the support 110 and the position is fixed, or the test is performed while the specimen 2 and the specimen holder 100 are fixed facing the front, and the positions of the specimen 2 and the specimen holder 100 are controlled during the test. In this case, the control unit can control the movement speed of the specimen holder through control of the support and the turntable.

When the test is performed in the fixed state, the aerosol passing through the specimen 2 is measured according to the position of the specimen holder 100. This is for simulating a posture of a user wearing clothes, and measures the inflow amount according to the direction.

When the specimen holder 100 moves in the polluted environment, the movement of the user is simulated, and the passage amount of aerosol is measured according to the tilted velocity, the rotational speed, or the like.

The control unit may control the position of the specimen holder and the face velocity at the same time to simulate various movements of a user.

Figure 3:
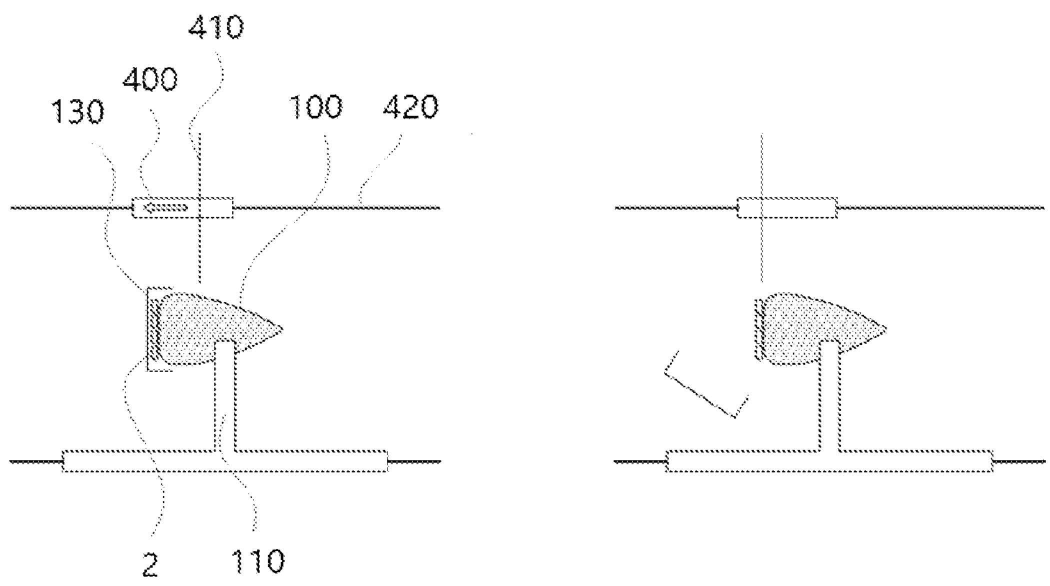
FIG. 3 is an exemplary diagram of a cover removal system of the present invention.
Figure 4A:
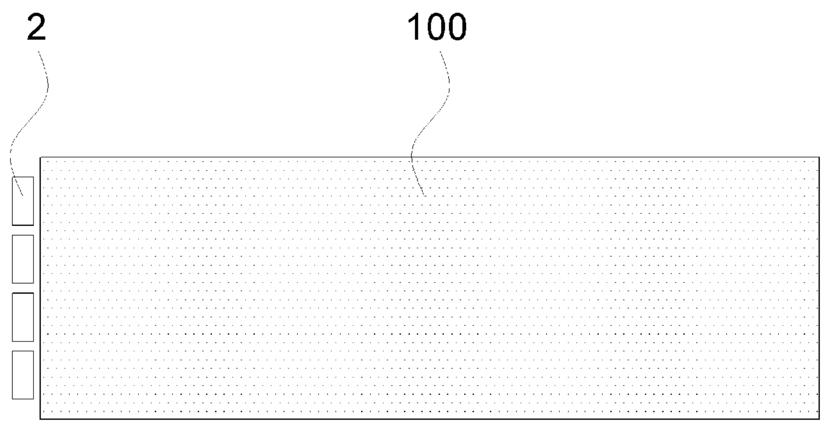
Figure 5B:
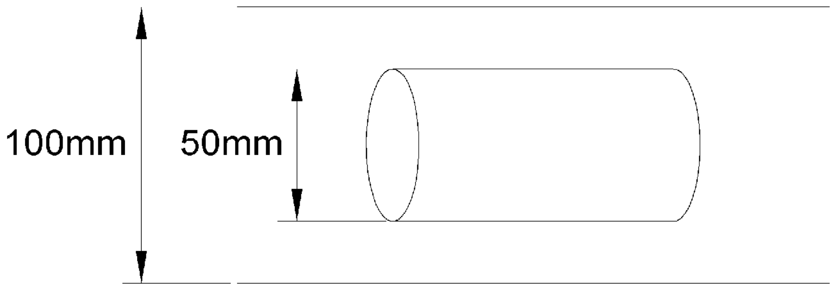
Figure 5C:
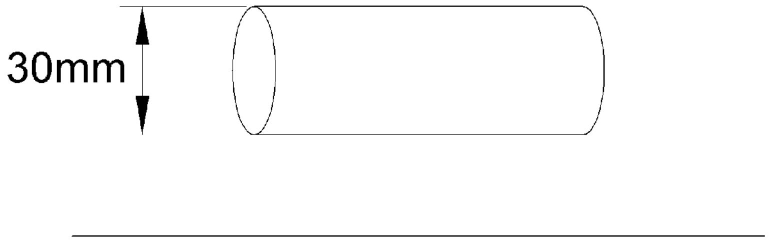
Figure 5D:
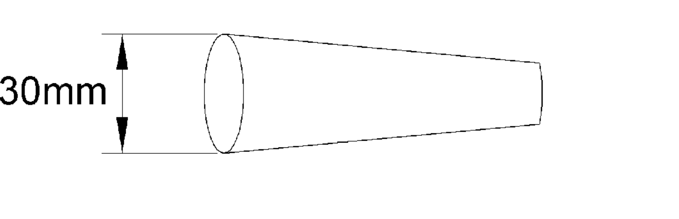
Figure 5E:
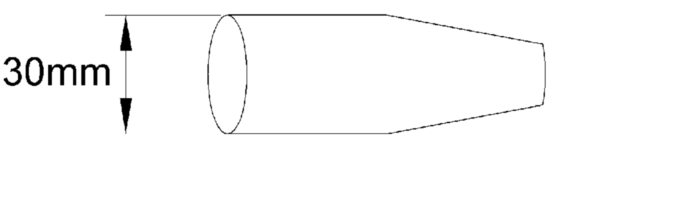

FIG. 3 is an exemplary diagram of a cover removal system of the present invention. Referring to FIG. 3, the cover 130 is arranged on the front of the specimen to prevent aerosol from reaching the specimen 2 before the test. When the cover 130 is arranged and the environment in which the aerosol of a certain concentration or more is measured is created inside the test unit 1, the cover 130 is removed by the cover removal device 400.

The cover removal device 400 is moved by the rail 420 arranged inside the test unit 1. The rail 420 is installed so that the cover removal device 400 moves in the longitudinal direction of the test unit 1 or moves along the inner circumferential surface of the test unit 1. The cover removal device 400 includes a guide 410 arranged to collide with the cover 130. The guide 410 moves within the cover removal device 400, and its length is controlled to contact the cover 130.

Through this, when the position of the specimen holder 100 is deformed by the support 110 and the turntable, there has an advantage in that the positions of the cover removal device 400 and the guide 410 may be changed to remove the cover 130. The cover removal device 400 is moved by a pre-entered program and automatically removes the cover 130 or is removed through manual manipulation.

The present invention analyzes the flow of aerosol according to the shape of the specimen holder. FIGS. 4A to 4D are exemplary diagrams of specimen holder deformation. Referring to FIGS. 4A to 4D, the specimen holder 100 is formed in a geometric shape. For example, it is formed into a cylindrical shape, a truncated cone shape, a mixture of a cylindrical shape and a truncated cone shape, a streamlined shape, and the like. The specimen 2 is arranged at one end of the specimen holder 100, and the other end has an open or closed shape. When the other end has an open shape, the aerosol flowing through the specimen 2 arranged at one end is discharged through the open other end. In addition, a vortex is formed according to the shape of the specimen holder 100, and the aerosol flows into the specimen holder 100 through the open other end.

FIGS. 5A to 5D are exemplary diagrams of a flow analysis model according to a shape of a specimen holder. In order to minimize the obstruction of the air flow of the test unit, design techniques for various types of specimen holder shapes are presented. In this case, the specimen is formed in a shape such as a circle or a square according to the specimen holder. In addition, in order for the specimen holder to have sufficient movement, the cross-sectional area of the specimen is limited to within 70% of the cross-sectional area of the test unit.

FIGS. 5A to 5D are exemplary diagrams illustrating models 1 to 4, respectively. Models 1 and 2 evaluate cylindrical specimen holders with diameters of 50 mm and 30 mm, respectively, to compare the flow analysis according to the cross-sectional area of the specimen holder. Model 3 evaluates the shape of a truncated cone with a diameter of 30 mm, and model 4 evaluates a mixed shape of a cylindrical shape with a diameter of 30 mm and a truncated cone shape to evaluate the flow according to the shape.

Figure 6A:
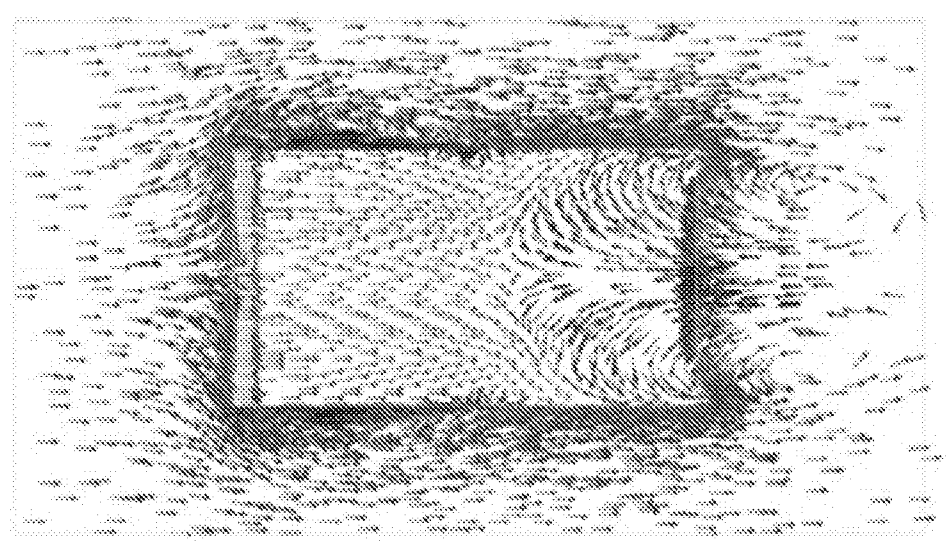
FIGS. 6A to 6D are exemplary diagrams of aerosol distribution flow analysis results according to the shape of the specimen holder.
Figure 6B:
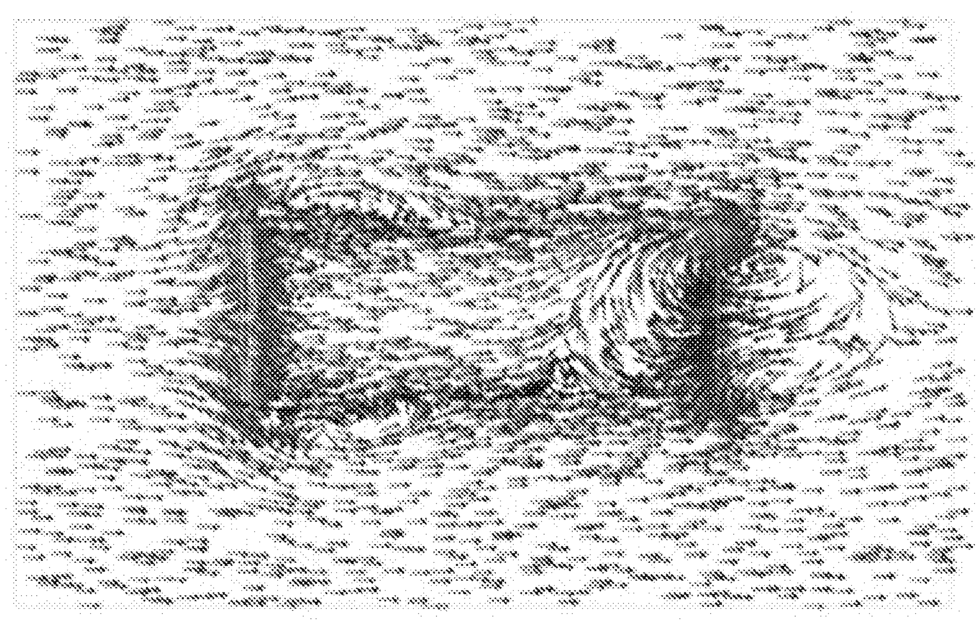
Figure 6C:
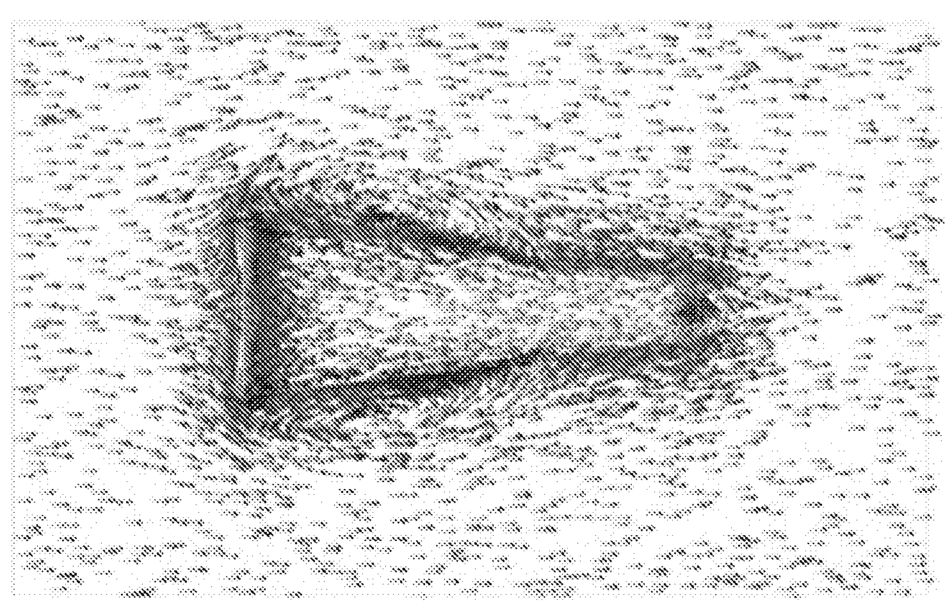
Figure 6D:
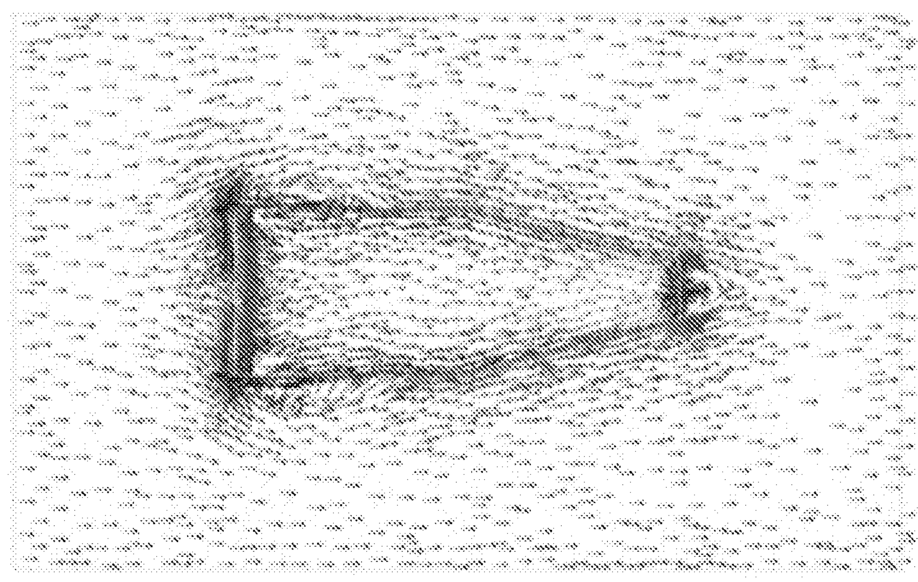

FIGS. 6A to 6D are exemplary diagrams of aerosol distribution flow analysis results according to the shape of the specimen holder. Referring to FIGS. 6A to 6D, the velocity vector distribution flow analysis results are illustrated, and FIGS. 6A and 6B illustrate that the flow direction of the fluid inside the specimen holder 100 is not formed in one direction as a whole, and the vortex phenomenon at the rear end of the specimen holder occurs. In the case of FIGS. 6C and 6D, there is little vortex phenomenon, showing a flow in a constant direction throughout the cell.

FIG. 7 is a diagram illustrating result data according to each analysis model. Referring to FIG. 7, it is a synthesis of the analytical model result data of models 1 to 4, and in the case of models 1 and 2, it is confirmed that negative pressure is generated at the rear end of the specimen through the measured outlet pressure. In addition, when comparing model 1 and model 2, it was confirmed that model 1, which has a large diameter, has faster face velocity. Models 3 and 4 confirm the results that almost no negative pressure is formed at the rear end of the specimen.

When comparing models 2 to 4 with the same diameter, it is confirmed that the flow rate is the same, but the passage flow rate ratio is higher in model 2.

It is used for dynamic simulation by using a test holder suitable for the environment required through flow analysis.

The present invention includes a method of evaluating protection performance using a dynamic swatch test cell device for evaluating aerosol protection performance of CBRN protection of flat specimens.

The method includes an arranging step in which a specimen holder having a specimen arranged at one end thereof is arranged in a test unit and a measuring step in which a fluid flows in one direction in the test unit, and a flow rate and a concentration of an agent are measured through a collection tube arranged at the front end and the inside of the specimen holder.

In the arranging step, the position of the specimen holder is changed by controlling the support coupled to the specimen holder. The support is composed of the multi-jointed arm or hinge, and the specimen holder is tilted and rotated. In addition, the lower end of the support may be rotated by being connected to the turntable.

The arranging step includes a cover coupling step in which a cover is arranged to surround the specimen, and the measuring step includes a cover removing step of removing the cover by the cover removing device after the required environment is created in the test unit. The cover blocks the fluid passing through the specimen before the test to prevent the aerosol from being attached to the specimen or from entering the inside of the specimen holder.

The arranging step includes a face velocity control step of controlling the face velocity by adjusting the internal pressure of the specimen holder by the pump connected to the rear end of the specimen holder. There is the advantage of simulating various postures and behaviors by controlling the internal pressure of the specimen holder.

In the measuring step, the position of the specimen holder is changed by controlling the support. There is the advantage of imitating the behavior of the movement by imparting the movement to the specimen holder during evaluation.

The present invention provides a practical protection performance test evaluation technology of CBRN protective clothing according to mass transfer characteristics of an aerosol, which is to break away from the existing static CBRN protection test cell and reflect an air flow around the CBRN protection and body motions of individual soldiers, and dynamically design a Swatch test cell in a geometric shape that can be installed inside a wind tunnel, and reflect an aerosol flow that can more closely simulate battlefield environment.

In addition, in the case of a specimen unit dynamic test cell of the present invention, the aerosol incident in the vertical direction of the existing test method is supplemented to measure aerosol transmittance, and the protection performance of the aerosol that can flow in various directions is evaluated to perform the aerosol protection performance evaluation that reflects the complex mass transfer characteristics of aerosols according to the body motions of the individual soldier and the air flow.

In addition, according to the present invention, it is possible to perform the aerosol protection performance evaluation according to the situations by attaching and detaching a tube connected to a pump at a rear end of the test cell so that a face velocity of the aerosol passing through the protective clothing can be adjusted if necessary.

In addition, according to the present invention, it is possible to more reliably perform the aerosol test evaluation by reflecting the automatic attachment and detachment system of the front cover of the protection clothing to start the test immediately after the aerosol flow environment reaches a steady state in the wind tunnel.

In addition, according to the present invention, it is possible to contribute to developing a test cell design technology that can more practically and reliably evaluate permeation or filtration performance for gas phases such as chemical agents or industrial toxic gases, radioactive particles or biological agent particles and various types of technologies in the civilian industry (environmental purification and filtration technology, medical and bioindustry technology, energy and material industry, etc.), military weapon systems, etc., through the provision of test and evaluation technology.

The present invention is not limited to the abovementioned exemplary embodiments, but may be variously applied, and may be variously modified without departing from the gist of the present invention claimed in the claims.

What is claimed is:

1. A device for evaluating protection performance including a test unit in which a fluid flows through the test unit in one direction from upstream to downstream, the device comprising:

a specimen holder arranged in the fluid flow within the test unit; and having at least one specimen arranged at an upstream end of the specimen holder;

a support having one end coupled to the specimen holder and the other end coupled to the test unit, the support is a multi-jointed arm configured to tilt and rotate the specimen holder at various angles relative to the fluid flow or the support is configured as an arm comprising at least one hinge to tilt the specimen holder at various angles relative to the fluid flow;

a plurality of collection tubes;

at least one of the plurality of collection tubes arranged upstream of the specimen holder and at least another of the plurality of collection tubes being arranged inside the specimen holder; and a control unit controlling the support.

2. The device of claim 1, wherein a turntable is arranged at a lower end of the support of the arm comprising the at least one hinge configured to rotate the support.

3. The device of claim 1, wherein the specimen holder is in a shape of a cylindrical shape, a truncated cone shape, a streamlined shape, or a mixed shape.

4. The device of claim 1, wherein the at least the another of the collection tubes arranged inside the specimen holder is made of a flexible material.

5. The device of claim 1, wherein a downstream end of the specimen holder is connected to a connector coupled to a pump, and the control unit is connected to the pump to control an internal pressure of the specimen holder.

6. The device of claim 5, wherein the connector is configured to be detachably connected to the specimen holder.

7. The device of claim 1, wherein the specimen holder includes a cover arranged to surround the at least one specimen and a cover removal device coupled to the test unit and configured to collide with the cover to remove the cover.

8. The device of claim 7, wherein the cover removal device includes a guide coupled to the cover removal device.

9. The device of claim 7, wherein the test unit includes a rail formed in a longitudinal direction of the test unit or a rail formed in a circumferential direction of the test unit, and the cover removal device is moved along the rail formed in a longitudinal direction of the test unit or the rail formed in a circumferential direction of the test unit.

10. The device of claim 9, wherein the cover removal device includes a guide coupled to the cover removal device.

11. A method of evaluating protection performance of protective clothing with a test unit, the method comprising:

establishing a required fluid flow environment within the test unit wherein the fluid contains an aerosol agent and flows in only one direction from upstream to downstream;

arranging a specimen holder within the test unit having a specimen arranged at an upstream end of the specimen holder; and measuring a flow rate and a concentration of the aerosol agent through at least one collection tube arranged upstream of the specimen holder and through at least another collection tube arranged inside of the specimen holder, wherein in the arranging step, a control unit controls a support coupled with the specimen holder to change a position of the specimen holder relative to the fluid flow;

wherein the arranging step further includes arranging a cover over the specimen, and after the required fluid flow environment within the test unit is established, removing the cover over the specimen.

12. The method of claim 11, wherein the arranging step includes a face velocity control step in which the control unit controls a pump connected to a downstream end of the specimen holder to adjust an internal pressure of the specimen holder and to control a face velocity of the fluid passing through the specimen.

13. The method of claim 11, wherein, in the measuring step, the control unit controls the support to change the position of the specimen holder relative to the fluid flow.

* * * * *